(12) United States Patent
Derkach

(10) Patent No.: US 9,556,173 B2
(45) Date of Patent: Jan. 31, 2017

(54) METHOD FOR PREPARATION OF 1-CYCLOPROPYL-6-FLUORO-1,4-DIHYDRO-8-METHOXY-7-[(AS,7AS)-OCTAHYDRO-6H-PYRROLO[3,4-B]PYRIDIN-6-YL]-4-OXO-3-QUINOLINECARBOXYLIC ACID

(71) Applicant: Nataliia Mykolaivna Derkach, Kiev (UA)

(72) Inventor: Nataliia Mykolaivna Derkach, Kiev (UA)

( * ) Notice: Subject to any disclaimer, the term of this patent is extended or adjusted under 35 U.S.C. 154(b) by 0 days.

(21) Appl. No.: 14/890,445

(22) PCT Filed: Jun. 5, 2013

(86) PCT No.: PCT/UA2013/000055
§ 371 (c)(1),
(2) Date: Jan. 27, 2016

(87) PCT Pub. No.: WO2014/185881
PCT Pub. Date: Nov. 20, 2014

(65) Prior Publication Data
US 2016/0159788 A1 Jun. 9, 2016

(30) Foreign Application Priority Data

May 13, 2013 (UA) .............................. A 201305962

(51) Int. Cl.
*C07D 471/04* (2006.01)

(52) U.S. Cl.
CPC .............. *C07D 471/04* (2013.01); *Y02P 20/55* (2015.11)

(58) Field of Classification Search
CPC .................................................. C07D 471/04
See application file for complete search history.

(56) References Cited

FOREIGN PATENT DOCUMENTS

| | | |
|---|---|---|
| DE | 4200414 A1 | 1/1992 |
| EP | 0167763 A1 | 5/1985 |
| EP | 0550903 A1 | 12/1992 |
| UA | 41323 C2 | 12/1994 |

OTHER PUBLICATIONS

Marks, Bloorg & Med CHem Lett, vol. 21, 4585-4588, 2011.*

* cited by examiner

*Primary Examiner* — D M Seaman
(74) *Attorney, Agent, or Firm* — Brown & Michaels, PC

(57) ABSTRACT

This invention relates to methods for preparation of chemical compound 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid, which comprise addition of heterocyclic amine containing protecting group, to ethyl-3-oxo-3-(2,4,5-trifluoro-3-methoxyphenyl)propanoate, followed by interaction with triethyl orthoformate, addition of cyclic amine, subsequent cyclization and formation of target product. The method for preparation claimed is technologically simple in comparison with analog and requires no special complex technical operations, which in its turn simplifies method for preparation of this chemical compound, and reduces cost of the final product, while the commercial production utilizing the method claimed has low degree of environmental threat.

5 Claims, 3 Drawing Sheets

METHOD FOR PREPARATION OF 1-CYCLOPROPYL-6-FLUORO-1,4-DIHYDRO-8-METHOXY-7-[(AS,7AS)-OCTAHYDRO-6H-PYRROLO[3,4-B]PYRIDIN-6-YL]-4-OXO-3-QUINOLINECARBOXYLIC ACID

FIELD OF INVENTION

The invention disclosed relates to the methods for preparation of chemical compound 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid.

PRIOR ART

Derivatives of quinolone carboxylic acid are widely used as synthetic antibacterial drugs in medicine. Compounds from the group of fluoroquinolones possess bactericidal action and demonstrate activity against wide spectrum of gram-positive and gram-negative microorganisms, anaerobic, acid-fast and atypical bacteria: *Mycoplasma* spp., *Chlamydia* spp., and *Legionella* spp. Antimicrobial means on basis of 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid are efficient towards most of microorganism strains resistant to beta-lactam antibiotics and macrolides.

Methods for preparation of 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid compounds are described in application DE 42004144 A1 (published 15 Jul. 1993). The compound is obtained with two methods.

In the first method, 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid is obtained from salts of quinolone- and naphthyridonecarboxylic acid derivatives (acid addition salts, alkali salts, alkaline earth salts, silver and guanidine salts of corresponding acids) comprising cyclic amines, by interaction with halogen containing compounds, in the presence of acid binding agents.

In the second method, the same quinolonecarboxylic acid derivatives are subjected to interaction with Michael acceptor, for example, acetylenedicarboxylic acid dialkyl ester, propiolic acid allyl ester. In these methods, racemic intermediate compounds interact with enantiomerically pure auxiliary reagent, diastereomers obtained are separated by chromatography, and auxiliary chiral group in diastereomer obtained is removed again. Racemic bicyclic amines are able to be converted via interaction with enantiomerically pure acids or sulfonic acids into a mixture of diastereomeric salts, which are separated by fractional crystallization into diastereomerically pure salts. Molar ratio of amine and enantiomerically pure acid may vary in a wide range. Treatment of these salts with hydroxides of alkali and alkaline earth metals allows to separate enantiomerically pure amines. Cleavage of racemates of principal intermediate compounds formed during preparation of racemic bicyclic amines with enantiomerically pure acids is performed in a similar manner. Racemic amines and intermediate compounds may be separated chromatographically on chiral support, may be converted by chemical binding with chiral acyl residue into a mixture of diastereomers, which are separated by distillation, crystallization or chromatography into diastereomerically pure acyl derivatives, wherefrom enantiomerically pure amines are obtained by saponification. Said methods have a drawback consisting in that the process of methods implementation results in the formation of both racemic mixture of intermediate compounds and racemic mixture of final compounds, thus necessitating chromatographic separation, which in its turn requires large expenditure of solvents and time.

There is known a method for preparation of 3-quinolinecarboxylic acid derivatives, wherein compounds of the general formula

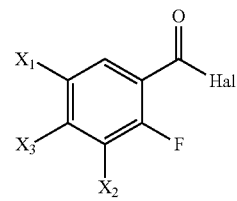

are subjected to interaction with malonic acid diethyl ester in the medium of solvent in the presence of magnesium methylate affording corresponding esters, wherein corresponding substituents $X_1$, $X_2$, $X_3$, and Hal, representing different substituents, including chloro, fluoro, and methoxy group, may be the same or different, and then submitted to partial saponification and decarboxylation in an aqueous medium in the presence of catalytic amounts of sulfuric acid or p-toluenesulfonic acid. The compounds obtained are subjected to interaction with triethyl ester of orthoformic acid in the presence of acetic anhydride. The intermediate compounds formed are further subjected to interaction with cyclopropylamine, followed by the step of cyclization, after which necessary amine is attached (EP application No. 0167763 A1, published 15 Jan. 1986). The drawback of this method lies in unsatisfactory yield of the product. Besides, alkaline saponification may result in side products able to form polymers, which is undesirable. Also, saponification under acidic conditions results in hydrogen fluoride release, leading to corrosion of production plant and product contamination with metal fluoride complexes. Patent for the invention UA 41323 C2 describes a method for preparation of 3-quinolonecarboxylic acid derivatives comprising steps of acid halide interaction with carboxylic acid ester in a solvent in the presence of alkaline agent, interaction with heterocyclic amine, alkaline saponification and product isolation in a free form or in the form of salts. Acid halide of the

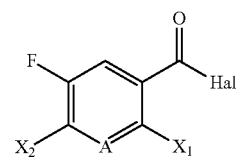

wherein $X_1$, $X_2$, and Hal are chloro or fluoro, and A denotes CH, CF, CCl, are subjected to saponification with aminoacrylic acid, then with cyclopropylamine, and subsequent saponification resulting in cyclization taking place in the presence of potassium carbonate. Each step is conducted without preliminary isolation and purification of intermediate products. The following compound is used as heterocyclic amine:

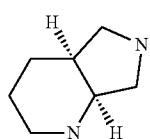

Isolation of the final product is performed in such a way that after alkaline saponification the reaction mixture is neutralized with acid and separated from the product obtained. The drawback of this method lies in that the interaction with acrylic acid ester results in side products capable of entering addition reactions with unsaturated bond of acrylic acid affording polymerization products, which are poisonous and explosive. In addition to that, carrying out of the following steps of the method without isolation and purification of intermediate products results in formation of a mixture of side products, which can participate in subsequent steps of the method, resulting in turn in the formation of small quantity of the final product. The final product contains considerable amounts of impurities and so necessitates substantial expenses in order to isolate it from impurities. Thus, realization of the method requires considerable expenses for reagents, solvents, and is technologically complex.

DISCLOSURE OF THE INVENTION

The invention is aimed at improvements in the method of producing compound 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid by changing actions and reagents in the method for preparation of said compound.

The problem is solved with method for preparation of 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid, comprising steps of:

(1) introduction into compound of formula (1)

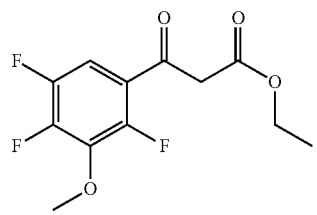

(1)

of tert-butyloctahydro-1H-pyrrolo[3,4b]pyridine-1-carboxylate affording compound of formula (2)

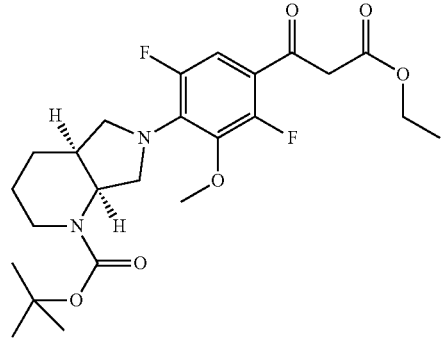

(2)

(2) interaction of compound (2) with alkyl orthoformate (preferred triethyl orthoformate) in acetic anhydride affording compound of formula (3)

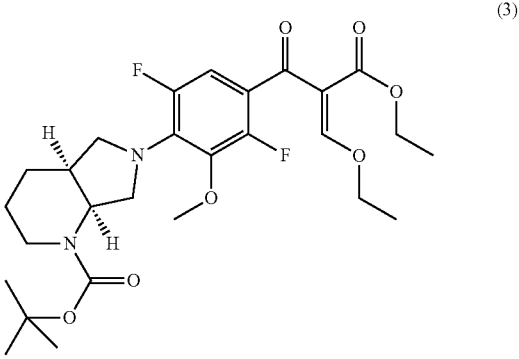 [SMILES: CCO/C=C(\C(=O)OCC)C(=O)c1cc(F)c(N2C[C@@H]3CCCN(C(=O)OC(C)(C)C)[C@@H]3C2)c(OC)c1F]

(3)

(3) addition of cyclic amine to the compound of formula (3) affording compound of formula (4)

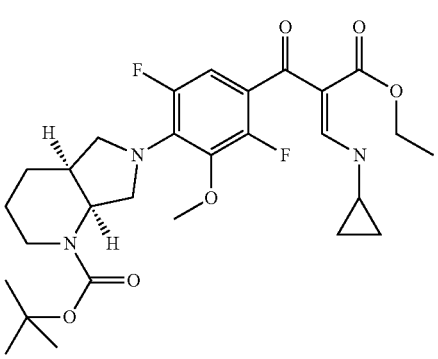

(4)

(4) cyclization of the compound of formula (4) in alcaline conditions affording compound of formula (5)

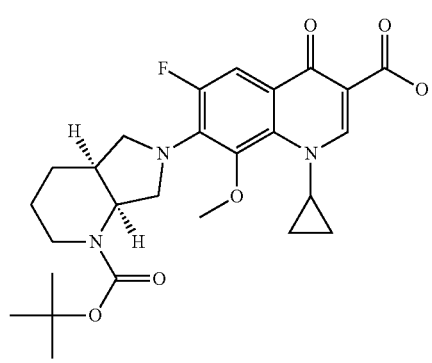

(5)

(5) cleavage of Boc protecting group from the compound of the formula (5) affording final compound of formula (6)

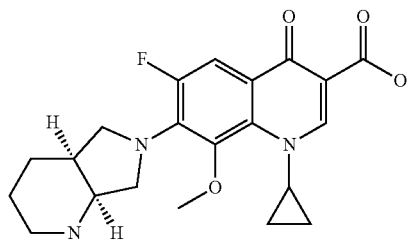

(6)

Furthermore, in the method claimed step (1) may be conducted in the presence of a base.

Furthermore, in the method claimed step (2) may be conducted in acetic anhydride at 130° C.

Furthermore, in the method claimed step (3) may be conducted at room temperature.

Furthermore, in the method claimed step (4) may be performed in the presence of 3N potassium hydroxide at 50° C.

EMBODIMENT(S) OF THE INVENTION

Figure 1:
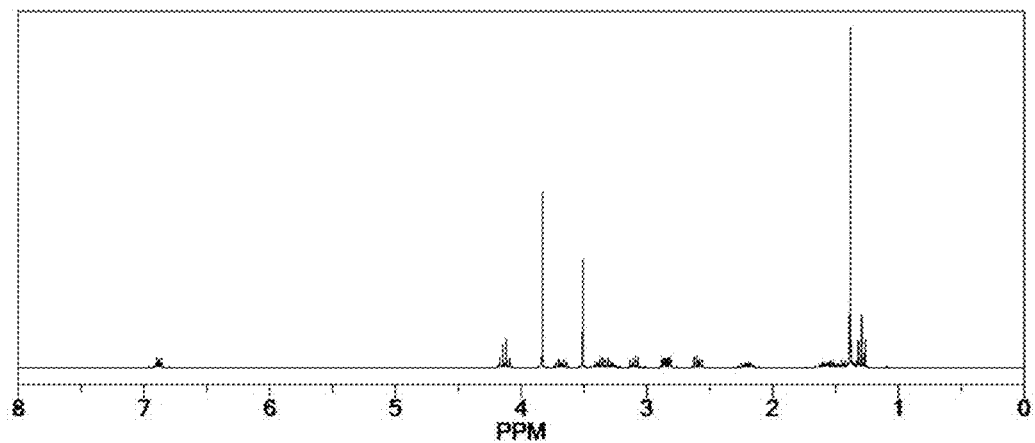
FIG. 1 is a spectrum of compound (4AS,7aS)-tert-butyl-6-(4-(3-ethoxypropanol)-3,6-difluoro-2-methoxyphenyl)octahydro-1H-pyrrolo[3,4-b]pyridine-1-carboxylate.

Step (1) comprises an action, such as addition of chiral amine, in this case (4AS,7aS)-tert-butyloctahydro-1H-pyrrolo[3,4-b]pyridine-1-carboxylate, to ethyl-3-oxo-3-(2,4,5-trifluoro-3-methoxyphenyl)propanoate (1) affording (4AS,7aS)-tert-butyl-6-(4-(3-ethoxypropanol)-3,6-difluoro-2-methoxyphenyl)octahydro-1H-pyrrolo[3,4-b]pyridine-1-carboxylate (2).

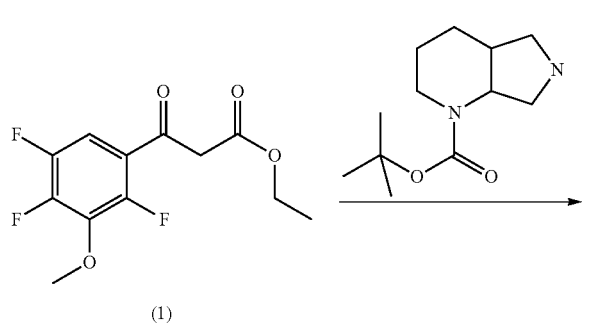

(1)

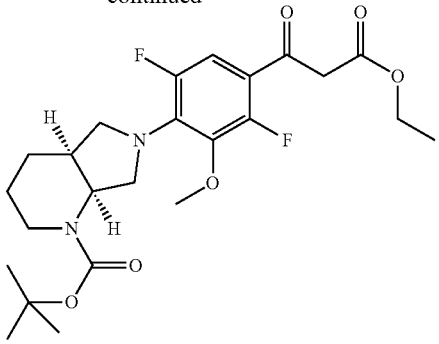

(2)

Protecting group in amine may be chosen from the group consisting of alkoxycarbonyl group, arylalkoxycarbonyl group, acyl group, alkoxyalkyl group or substituted silyl group. No special limitations are imposed on the type of the amino-protecting group, and some groups may be utilized in reaction until they begin inhibit interaction between compound (1) and amino compound. Advantageously used are tert-butoxycarbonyl group and 2,2,2-trichloroethoxycarbonyl, tert-butoxycarbonyl group being preferred. One or more amine equivalent is utilized in the reaction. The reaction is carried out in the presence of a base, since HF is produced in this step, which may inhibit reaction with compound (1) by forming amine salt.

Step (2) comprises an action, such as interaction of compound (2) with alkyl orthoformate in acetic anhydride resulting in formation of the compound of formula (3).

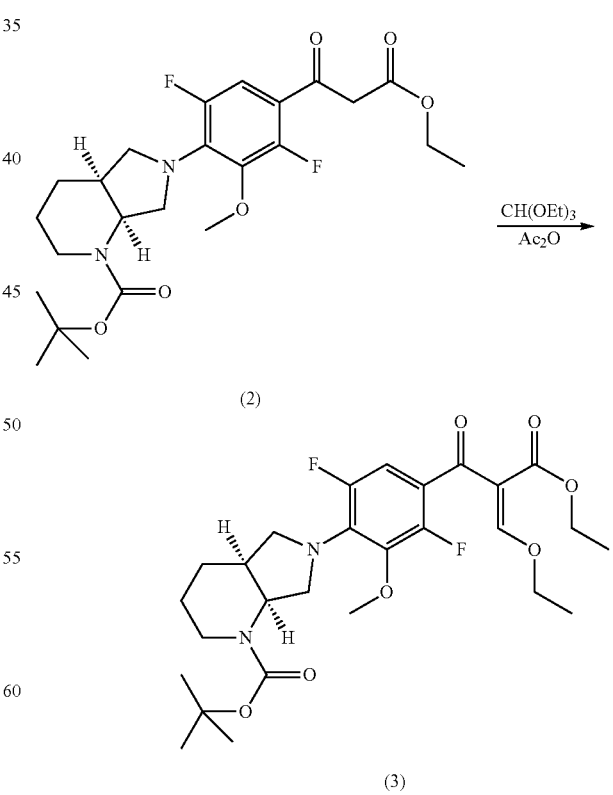

Alkyl orthoformate and acetic anhydride are used in equivalent amounts. Alkyl orthoformate may contain one to six alkyl groups. Preferred compounds are triethyl orthoformate and trimethyl orthoformate. Alkyl orthoformate is utilized as reagent and solvent simultaneously. Reaction is carried out in the temperature range from room temperature to the boiling point of solvent for one to six hours.

Step (3) comprises interaction of the compound of formula (3) with cyclic amine affording compound of formula (4).

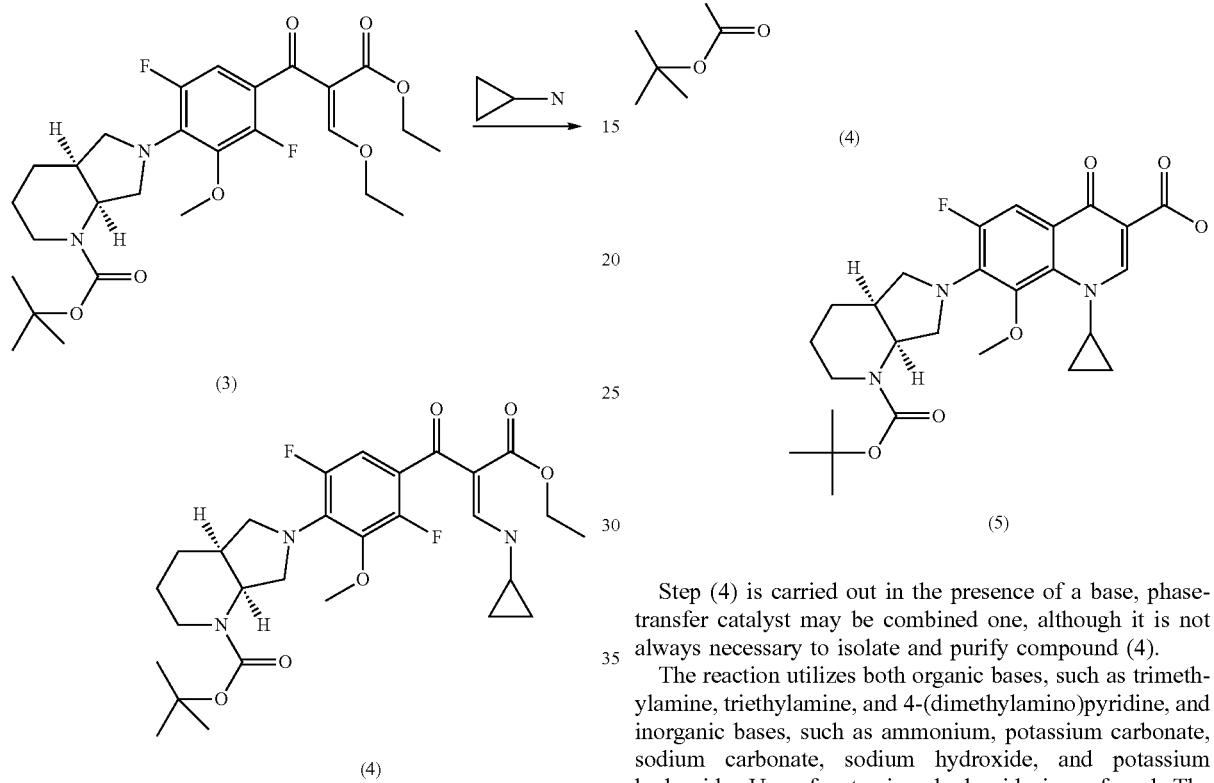

Reaction is carried out in the presence of base, which may be chosen from the group of organic bases, for example, trimethylamine, triethylamine, and 4-(dimethylamino)pyridine, and inorganic bases, such as ammonium, potassium carbonate, sodium carbonate, sodium hydroxide, and potassium hydroxide. Preferred are tertiary amines, in particular, triethylamine Amine compound may be an acid salt. The acid salt may be formed by inorganic acids, such as hydrochloric acid, sulfuric acid, nitric acid, hydrobromic, hydrofluoric, hydroiodic acids, as well as organic acids, such as toluenesulfonic, benzenesulfonic, methanesulfonic (sulfonic acid may contain halogen atom or alkyl group as a substituent), trifluoroacetic acid, maleic and fumaric acids. There are also no limitations in choosing solvent, and many solvents are utilized until they begin to inhibit the reaction. It is possible to use toluene, N,N-dimethylacetamide, N,N-dimethylformamide, dimethylsulfoxide, and N-methylpyrrolidone. Particularly preferred is toluene. Reaction is conducted at room temperature for 30 minutes to 6 hours, depending on formation of the final product and consumption of the initial compounds.

Step (4) comprises cyclization of the compound of formula (4) affording compound of formula (5):

Step (4) is carried out in the presence of a base, phase-transfer catalyst may be combined one, although it is not always necessary to isolate and purify compound (4).

The reaction utilizes both organic bases, such as trimethylamine, triethylamine, and 4-(dimethylamino)pyridine, and inorganic bases, such as ammonium, potassium carbonate, sodium carbonate, sodium hydroxide, and potassium hydroxide. Use of potassium hydroxide is preferred. The base is advantageously used in an amount necessary to capture hydrogen fluoride generated at ring closure, and to hydrolize the ester. The base may be added directly into the reaction mixture or it may be added into the reaction mixture as an aqueous solution. Base or solution is not a required form of admixture with the reaction solvent.

Solvents used include toluene, N,N-dimethylacetamide, N,N-dimethylformamide, dimethylsulfoxide, and N-methylpyrrolidone. Use of toluene is preferred. Tetrabutylammonium bromide is used as catalyst. The reaction may be conducted in the temperature range from room temperature to boiling point of the reaction mixture. Time of reaction depends on time of conversion of initial compounds into the final ones and may be from one to 24 hours.

In carrying out the method claimed, compound (5) may be isolated and purified by common techniques. In one method, pH of the reaction mixture is adjusted by the addition of corresponding acid, and the mixture is agitated while cooled with ice. The crystals precipitating are filtered off. In another method, pH of the reaction mixture is adjusted by addition of corresponding acid and addition of corresponding solvent into the reaction mixture to isolate this particular compound. The extract obtained is concentrated and compound (5) is recrystallized from corresponding solvent. The compound (5) is obtained in a free form or in a salt form. The examples of salts include salts of inorganic acids, such as hydrochloric acid, sulfuric acid, nitric acid, hydrobromic, hydrofluoric, and hydroiodic acids, as well as salts of organic acids, such as toluenesulfonic, benzenesulfonic, methanesulfonic, trifluoroacetic acid, trichloroacetic acid, acetic acid, formic acid, fumaric acid, and salts of alkaline metals and alkaline earth metals, such as sodium, potassium, calcium or lithium. Even if the compound is a mixture of free form and salt, the compound may be isolated in the solvate form. Solvate may be formed with water, ethanol, propanol, acetonitrile, acetone, or may be formed by water absorption.

Step (5) is carried out by cleavage of tert-butylcarboxylate from the compound of formula (5) affording compound of formula (6):

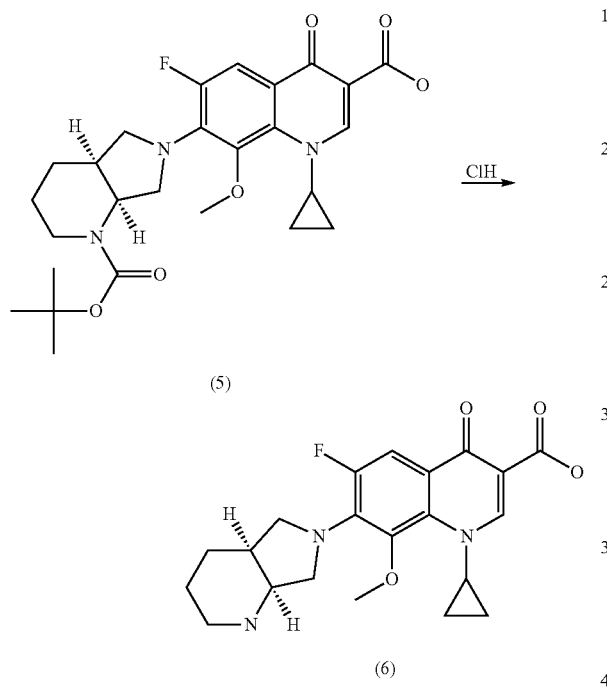

Step (5) is conducted in solvent on heating with hydrochloric acid.

Below are presented examples demonstrating one of the possible embodiments of the method for preparation claimed of the compound 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid.

EXAMPLE 1

Preparation of (4AS,7aS)-tert-butyl-6-(4-(3-ethoxypropanol)-3,6-difluoro-2-methoxyphenyl)octahydro-1H-pyrrolo[3,4-b]pyridine-1-carboxylate (4AS,7aS)-tert-butyloctahydro-1H-pyrrolo[3,4-b]pyridine-1-carboxylate (4.10 g, 18.1 mmol) was added to the solution containing ethyl-3-oxo-3-(2,4,5-trifluoro-3-methoxyphenyl)propanoate (5 g, 18.1 mmol), acetonitrile (50 ml), and triethylamine (5.1 ml, 2 eq.), and mixture was agitated at 25° C. for three days and at 50° C. for 4 hours. After that, the reaction mixture was cooled, and solvent was evaporated at reduced pressure. To the residue were added toluene (50 ml) and saturated brine (30 ml). The organic residue was dried over magnesium sulfate, and the solvent was removed at reduced pressure. The compound was obtained as a yellow-green substance 7.295 g (84%).

The compound has been identified by physico-chemical methods. NMR spectrum of the compound is presented in FIG. 1.

EXAMPLE 2

Preparation of (4aS,7aS)-tert-butyl-6-(4-((Z)3-ethoxy-2-(ethoxycarbonyl)-acryloyl)-3,6-difluoro-2-methoxyphenyl)octahydro-1H-pyrrolo[3,4-b]pyridine-1-carboxylate (4AS,7aS)-tert-butyl-6-(4-(3-ethoxypropanol)-3,6-difluoro-2-methoxyphenyl)octahydro-1H-pyrrolo[3,4-b]pyridine-1-carboxylate (1.033 g, 2.14 mmol) was dissolved in acetic anhydride (1.21 ml, 6 eq.) and triethyl orthoformate (2.13 ml, 6 eq.). The reaction mixture was agitated for 14 hours at 130° C. After that, the reaction mixture was cooled, and solvent was removed at low pressure. To the residue was added toluene (10 ml), and the reaction mixture was boiled twice. The acetic acid present in the liquid was neutralized with sodium bicarbonate, and inorganic product formed was filtered off. The solvent remaining after filtration was removed at reduced pressure leaving a yellow-orange sediment, 933 mg (81%).

Figure 2:
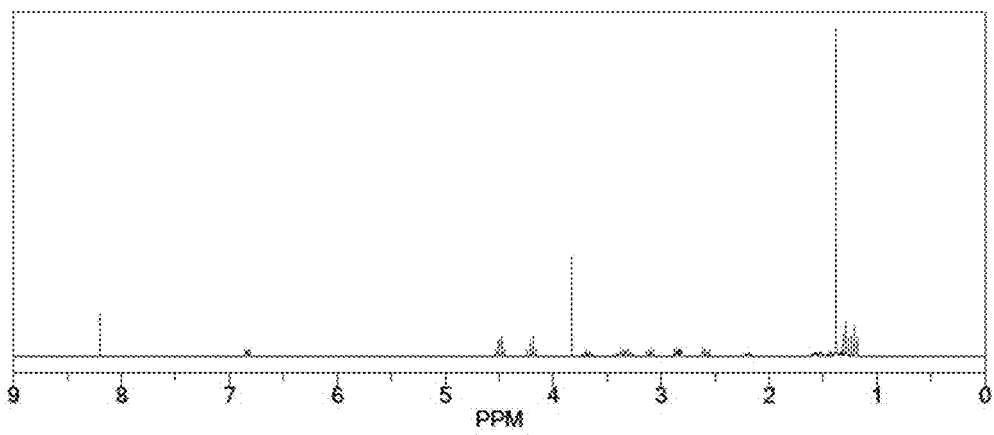
FIG. 2 is a spectrum of compound (4aS,7aS)-tert-butyl-6-(4-((Z)3-ethoxy-2-(ethoxycarbonyl)acryloyl)-3,6-difluoro-2-methoxyphenyl)octahydro-1H-pyrrolo[3,4-b]pyridine-1-carboxylate.
Figure 3:
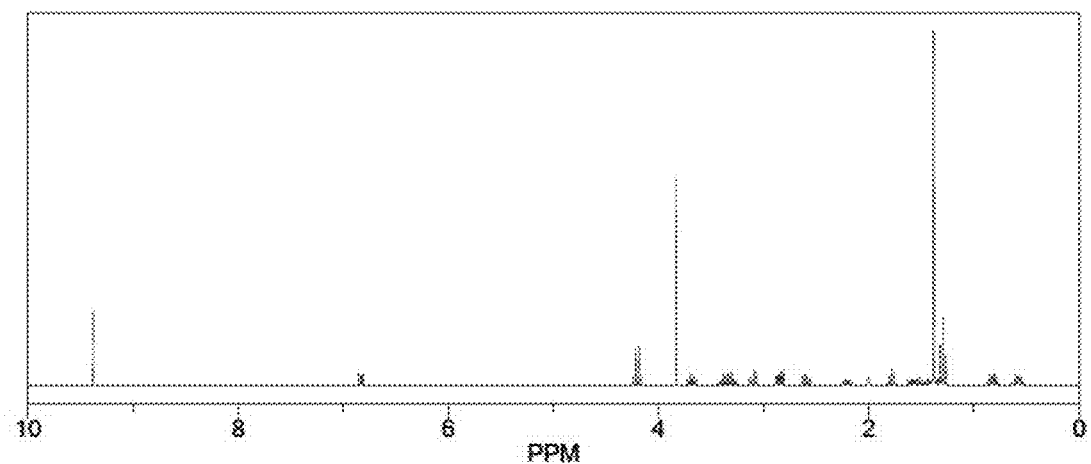
FIG. 3 is a spectrum of compound (4aS,7aS)-tert-butyl-6-(4-((Z)3-cyclopropylamino)-2-(ethoxycarbonyl)acryloyl)-3,6-difluoro-2-methoxyphenyl)octahydro-1H-pyrrolo[3,4-b]-pyridine-1-carboxylate.

The compound has been identified by physico-chemical methods. NMR spectrum of the compound is presented in FIG. 2.

EXAMPLE 3

Preparation of (4aS,7aS)-tert-butyl-6-(4-((Z)3-cyclopropylamino)-2-(ethoxycarbonyl)-acryloyl)-3,6-difluoro-2-methoxyphenyl)octahydro-1H-pyrrolo[3,4-b]pyridine-1-carboxylate Cyclopropylamine (390 mg, 6.83 mmol) was added to the solution containing (4aS,7aS)-tert-butyl-6-(4-((Z)3-ethoxy-2-(ethoxycarbonyl)acryloyl)-3,6-difluoro-2-methoxyphenyl)-octahydro-1H-pyrrolo[3,4-b]pyridine-1-carboxylate (787 mg, 1.45 mmol), toluene (15.2 ml), and triethylamine (0.22 ml, 1.1 eq.). The reaction mixture was stirred for 10 minutes at 25° C. The organic residue was washed with water (10 ml×2) and brine (10 ml), and dried over magnesium sulfate. Solvent was removed at reduced pressure. (4aS,7aS)-tert-butyl-6-(4-((Z)3-cyclopropylamino)-2-(ethoxycarbonyl)acryloyl)-3,6-difluoro-2-methoxyphenyl)octahydro-1H-pyrrolo[3,4-b]pyridine-1-carboxylate, 789 mg (99%), was obtained as a yellow-orange substance.

EXAMPLE 4

Preparation of 7-((4aS,7aS)-1-tert-butoxycarbonyl)hexahydro-1H-pyrrolo[3,4-b]-pyridin-6-(2H)-yl)-1-cyclopropyl-6-fluoro-8-methoxy-4-oxo-1,4-dihydroquinoline-3-carboxylic acid Tetrabutylammonium bromide (TBAB, 8 mg) was added to the solution containing (4aS,7aS)-tert-butyl-6-(4-((Z)3-cyclopropylamino)-2-(ethoxycarbonyl)acryloyl)-3,6-difluoro-2-methoxyphenyl)octahydro-1H-pyrrolo[3,4-b]pyridine-1-carboxylate (736 mg, 1.34 mmol), toluene (14.8 ml), and 3N solution of potassium hydroxide (2.23 ml, 5 eq.), and the reaction mixture was stirred for 4 hours at 50° C. Another portion of 3N solution of potassium hydroxide (2.23 ml, 5 eq.) was added to the reaction mixture, and stirring continued for 2 hours. Then the reaction mixture was poured on ice, and slightly acidified with 3N hydrochloric acid solution to form a suspension, to which were added water (15 ml) and brine (5 ml) for separation. Aqueous residue was extracted with toluene (20 ml×2); this was made to recover organic components, and all organic layers were combined. The combined organic phases were dried over sodium sulfate, and solvent was removed by rotary evaporator at reduced pressure. Residue was crystallized, and solvent was removed at reduced pressure. After that, the residue was dissolved in toluene (1.5 ml) and hexane (15 ml). Mixture was stirred for 3 hours at 25° C. Precipitates obtained were filtered off and dried. As a result, 558 mg (83%) of the compound 7-(4aS,7aS)-1-tert-butoxycarbonyl) hexahydro-1H-pyrrolo[3,4-b]-pyridin-6-(2H)-yl)-1-cyclopropyl-6-fluoro-8-methoxy-4-oxo-1,4-dihydroquinoline-3-carboxylic acid was obtained as yellow-orange crystals.

Figure 4:
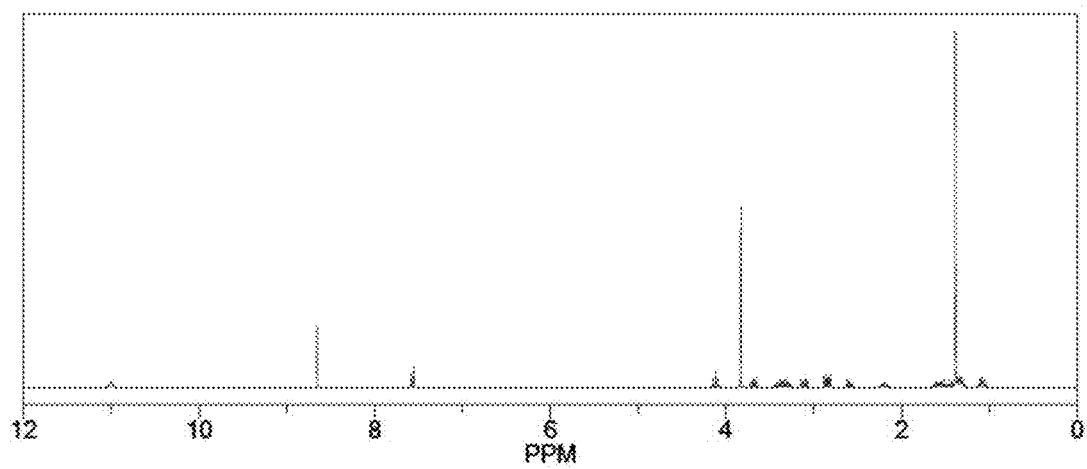
FIG. 4 is a spectrum of compound 7-((4aS,7aS)-1-tert-butoxycarbonyl)hexahydro-1H-pyrrolo[3,4-b]-pyridin-6-(2H)-yl)-1-cyclopropyl-6-fluoro-8-methoxy-4-oxo-1,4-dihydroquinoline-3-carboxylic acid.

Compound has been identified by physico-chemical methods. NMR spectrum of the compound is presented in FIG. 4.

EXAMPLE 5

Preparation of 1-cyclopropyl-6-fluoro-7-((4aS,7aS)-hexahydro-1H-pyrrolo[3,4-b]pyridin-6(2H)-yl)-8-methoxy-4-oxo-1,4-dihydroquinoline-3-carboxylic acid 7-((4aS,7aS)-1-tert-butoxycarbonyl)hexahydro-1H-pyrrolo[3,4-b]-pyridin-6-(2H)-yl)-1-cyclopropyl-6-fluoro-8-methoxy-4-oxo-1,4-dihydroquinoline-3-carboxylic acid was suspended in ethanol (727 mg, 1.45 mmol) at 22-30° C., treated with 21.70 mg of hydrochloric acid (37 wt. %) and heated under reflux for 2 hours. After completion of the conversion most of the alcohol was stripped. The salt of 1-cyclopropyl-6-fluoro-1,4-dihydro-8-methoxy-7-[(4aS, 7aS)-octahydro-6H-pyrrolo[3,4-b]pyridin-6-yl]-4-oxo-3-quinolinecarboxylic acid formed was precipitated, the solution was heated to 40° C., and dichloromethane was added. Precipitation of 1-cyclopropyl-6-fluoro-1,4-dihydro-8-methoxy-7-[(4aS,7aS)-octahydro-6H-pyrrolo[3,4-b]-pyridin-6-yl]-4-oxo-3-quinolinecarboxylic acid was conducted by dissolving hydrochloride salt in 1:1 mixture of solvents EtOH/water. 30% solution of sodium hydroxide was added in portions at 0-7° C. until pH has reached a value pH>12.5. After 4-48 hours the substance precipitated was filtered off, washed with water and dried in vacuo. The method affords a powder from white to yellowish colour, 518 mg (89%), with melting point 324-325° C.

Figure 5:
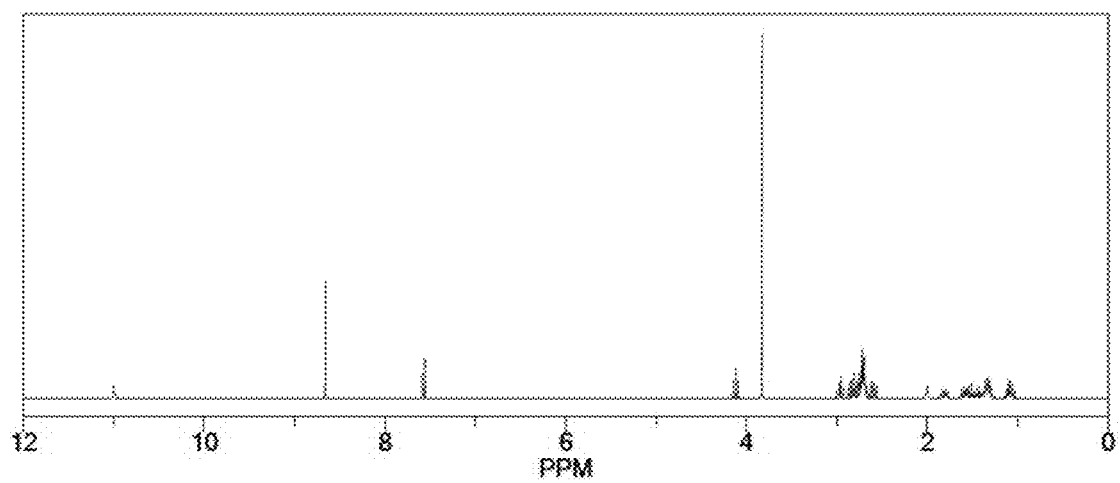
FIG. 5 is a spectrum of compound 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid.

Compound has been identified by physico-chemical methods. NMR spectrum of the compound is presented in FIG. 5.

It can be seen from the examples presented that in carrying out the method claimed of preparation of 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid, more easily accessible reactants are used, and in conducting stages of the method claimed as a result of addition, in the first stage, of chiral amine containing protecting group, no racemic mixtures are formed, which would require separation and purification on chromatographic column with silica gel. In this way, enantiomerically pure intermediate compounds are formed in the method claimed, which may be easily crystallized and purified, and used in subsequent stages. Due to this, yield is increased both of intermediate compounds and of the final product. Thus, the method claimed makes unnecessary additional expenses for solvents, silica gel, reagents, time, and is economically sound. The manufacturing operations themselves, as a rule, are conducted in normal conditions (without additional heating or considerable temperature decrease) and without necessity to strictly maintain pH values, and the method is realized without using costly solvents. The above results in the method for preparation claimed being technologically simple in comparison with analogue and requires no special complex technical operations, which in its turn simplifies the method for preparation of given chemical compound, and reduces cost of the final product, while the commercial production utilizing the method claimed has low degree of environmental threat.

The examples presented of the realization of the method claimed for preparation of 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid are intended only to illustrate the invention, and not to limit it.

The invention claimed is:

1. A method for preparation of a compound of formula (6)

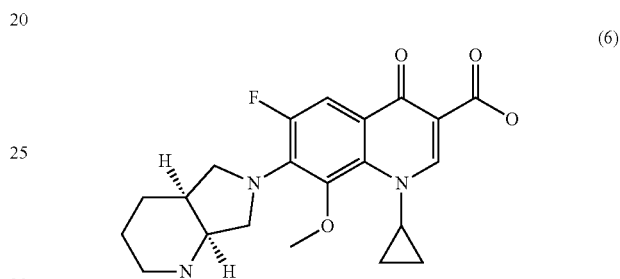

(6)

comprising the steps of:
a) mixing tert-butyloctahydro-1H-pyrrolo[3,4b]pyridine-1-carboxylate with the compound of formula (1)

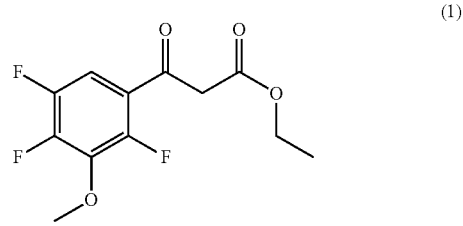 [SMILES: CCOC(=O)CC(=O)c1cc(F)c(F)c(OC)c1F]

(1)

to form a compound of formula (2)

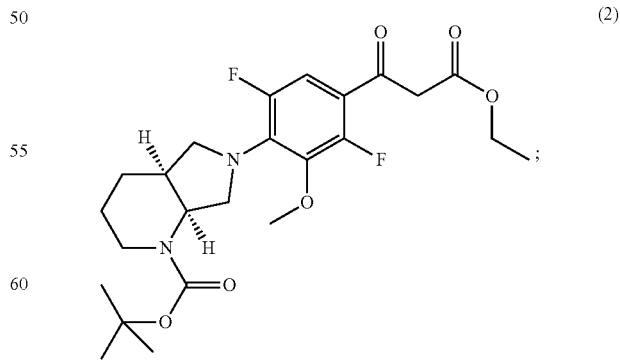

(2)

b) mixing the compound of formula (2) with triethyl orthoformate in acetic anhydride to form a compound of formula (3)

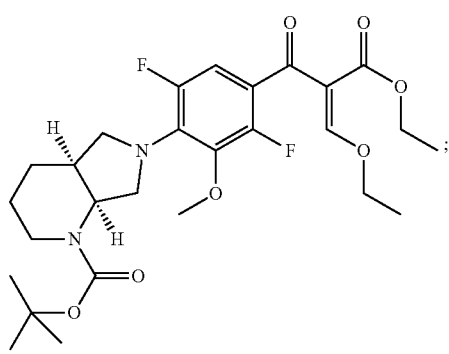

(3)

c) adding cyclic amine to the compound of formula (3) to form a compound of formula (4)

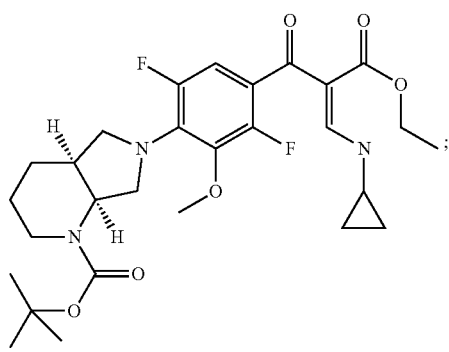

(4)

d) cyclizing the compound of formula (4) in alkaline conditions to form the compound of formula (5)

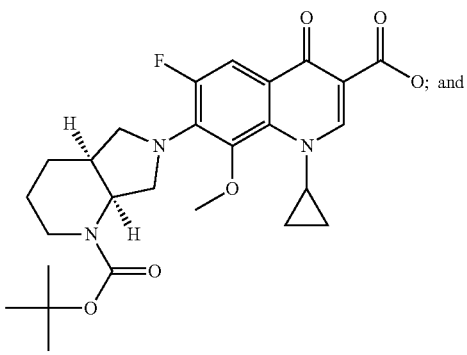

(5)

e) cleaving Boc protecting groups from the compound of formula (5) to form a final compound of formula (6)

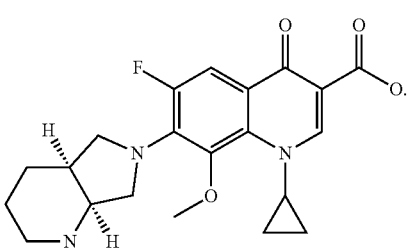

(6)

2. The method according to claim 1, characterized in that step a) is conducted in the presence of a base.

3. The method according to claim 1, characterized in that step b) is conducted in acetic anhydride at 130° C.

4. The method according to claim 1, characterized in that step c) is conducted at room temperature.

5. The method according to claim 1, characterized in that step d) is conducted in the presence of 3N potassium hydroxide at 50° C.

* * * * *